(12) United States Patent   (10) Patent No.: US 8,628,484 B1
Dolan et al.                     (45) Date of Patent: Jan. 14, 2014

(54) ORAL FUNCTION AND DYSFUNCTION QUANTIFICATION METHOD

(71) Applicants: John C. Dolan, New York, NY (US);
Brian L. Schmidt, New York, NY (US)

(72) Inventors: John C. Dolan, New York, NY (US);
Brian L. Schmidt, New York, NY (US)

(*) Notice: Subject to any disclaimer, the term of this patent is extended or adjusted under 35 U.S.C. 154(b) by 0 days.

(21) Appl. No.: 13/679,077

(22) Filed: Nov. 16, 2012

Related U.S. Application Data

(62) Division of application No. 12/378,085, filed on Feb. 11, 2009, now Pat. No. 8,343,077.

(51) Int. Cl.
*A61B 5/103*   (2006.01)
*A61B 5/117*   (2006.01)

(52) U.S. Cl.
USPC ................ 600/590; 600/587; 600/589

(58) Field of Classification Search
USPC ............. 600/557, 587, 589, 590, 595
See application file for complete search history.

(56) References Cited

U.S. PATENT DOCUMENTS

| 4,641,661 | A | * | 2/1987 | Kalarickal | 600/557 |
| 4,908,976 | A | * | 3/1990 | Dagenais | 43/58 |
| 5,027,547 | A | * | 7/1991 | Livshin | 43/124 |
| 5,941,833 | A | * | 8/1999 | Lipman | 600/555 |
| 6,098,334 | A | * | 8/2000 | Stouffer | 43/58 |
| 6,907,280 | B2 | * | 6/2005 | Becerra et al. | 600/407 |
| 8,343,077 | B1 | * | 1/2013 | Dolan et al. | 600/590 |

OTHER PUBLICATIONS

"The Collegiate Inventors Competition: 2007 Finalists". published online Dec. 22, 2007, accessed on Mar. 22, 2010 online at <<http://web.archive.org/web/20071222123206/http://www.invent.org/collegiate/finalists.html>>. pp. 7-8.*

* cited by examiner

*Primary Examiner* — Rene Towa
*Assistant Examiner* — Adam Eiseman
(74) *Attorney, Agent, or Firm* — Rodgers & Rodgers

(57) ABSTRACT

An oral function and dysfunction quantification method that automatically records the amount of time required for a laboratory animal to gnaw through multiple obstructions in a tube includes a confinement tube and spring-loaded polymer dowels that actuate timers to precisely record the time required for a rodent to complete a discrete gnawing task. The investigation of human orofacial pain requires an animal test that objectively measures impairment secondary to pain during an oral function (gnawing) that is analogous to behavior that elicits pain in human patients (chewing). The method can also evaluate behavioral change secondary to complex disorders such as anxiety and depression and facilitate evaluation of molecular mechanisms and pharmacologic therapies relevant to chronic orofacial pain and behavioral disorders.

8 Claims, 3 Drawing Sheets

ORAL FUNCTION AND DYSFUNCTION QUANTIFICATION METHOD

This is a division of patent application Ser. No. 12/378,085 filed Feb. 11, 2009.

BACKGROUND OF THE INVENTION

Orofacial (mastication and chewing) dysfunction is one of the hallmarks of orofacial pain. A method that measures such dysfunction in an animal model of pain would be of great utility in scientific testing of ideas concerning the mechanical and molecular mechanisms involved in pain and in evaluating drug efficacy for the treatment of orofacial pain. An objective animal assay that quantifies pain-induced dysfunction like that seen clinically in patients is not available. Most previous animal studies of orofacial pain evaluate a painful acute cutaneous stimulus e.g., heat in the head or neck of the animal rather than evaluating pain in animal models of conditions such as oral cancer, TMJ disorders, or muscle inflammation in the head and neck. One of the principle reasons that orofacial pathologies e.g., cancer or TMJ disorders are often not employed to elicit pain in these animal studies is that investigators have no objective assay or device to evaluate and quantify the forms of orofacial dysfunction that pain produces in these conditions. Previous animal studies have evaluated stereotyped behaviors (e.g., rubbing and flinching of the head) for use as indices of acute orofacial pain. Pain assays of stereotyped behaviors are not high throughput and not objective. In addition, they have not proven useful for objectively measuring chronic orofacial pain in animals. To infer pain in a model of chronic temporomandibular joint (TMJ) disorders or masticatory muscle pain, studies quantifying meal duration, meal size and inter-meal interval have been developed. These meal (feeding) studies are limited in their ability to resolve behavioral changes due to orofacial pain versus pain originating elsewhere in the body because rodents with non-trigeminal pain also demonstrate a reduced feeding rate. To show a significant difference between orofacial and non-trigeminal pain, investigators have looked at intermeal interval. However, intermeal interval is an even more indirect method of demonstrating oral dysfunction resulting from pain. All meal studies used to evaluate orofacial pain are fundamentally prone to error because they are potentially confounded by variables that affect appetite. Appetite can be altered by analgesics, systemic disease, time of day, duration of the study and reward associated with consumption. Moreover, pain that originates outside of the trigeminal system reduces appetite and affects feeding in humans and rodents. The limitations of meal (feeding) assays can be avoided by directly measuring gnawing function not associated with consumption. There is currently no automated method available that quantifies gnawing function to evaluate orofacial pain. A gnawing assay for mice was developed by Ayada et al. (Am J Physiol Regul Integr Comp Physiol 2000; 279(6):R2042-2047) whereby the mass of the material gnawed away from a plastic strip was used as a proxy for gnawing activity. Our assay measures an entirely different outcome variable (time to complete a discrete gnawing task) and our method, to carry out our assay does so in an automated fashion unlike the Ayada assay. No current or known automated method evaluates the character, duration or restriction of oral function in animals such that dysfunction secondary to a painful orofacial pathology in the animal is directly comparable to pain induced dysfunction in patients.

BRIEF SUMMARY OF THE INVENTION

The oral function and dysfunction quantification method, according to this invention, utilizes a device which objectively measures a task related behavior that can be used as a quantifiable behavioral index of pain in animal models of head and neck cancer pain, neuropathic pain, temporomandibular joint disorders, tooth pain and muscle inflammation. Since the method measures goal-directed behavior, it can be used to index and quantify behavioral changes secondary to complex conditions such as anxiety and depression. The method has the capacity to test hypotheses concerning the mechanical and molecular causes of pain, causes of complex behavioral disorders and to test the efficacy of pharmacologic agents to treat these disorders. It will allow investigators to objectively measure and compare orofacial function before and after experimental interventions.

This invention exploits a rodent's instinctual response to gnaw through an obstruction when confined in a narrow tube as first described by Ayada et al. (2000). These authors measured gnawing rate by quantifying the mass of plastic gnawed from a hard plastic confinement strip on the end of a narrow tube over a fixed period of time; the task is infinite since the strip is perpetually replaced by an investigator present during the entire experiment. Our method employs an automated mechanism that records the amount of time required for a mouse to gnaw through an obstruction and actually gain escape. This entails a discrete gnawing task requiring a fixed amount of gnawing effort because the rodent always gnaws though the dowel in a similar pattern after training and the device retracts both ends of the dowel from the tube the instant that it is severed. With our method, the presence of the investigator is not required during the measurement portion of the experiment nor immediately after the animal has gained escape from the device.

High throughput is a significant technical advantage of the invention. It is fully automated once the first timer is started and multiple devices can be run concurrently. Measurement of the outcome variable is objective and not prone to investigator bias. To accommodate instinctual proclivities of mice and other rodents, nocturnal prey animals, the device is employed in darkness in the absence of the investigator. Initial delay due to habituation, animal loading inconsistencies, or drug side effects is less likely to affect the outcome measure since only the gnaw times for the second dowel (or, if present, subsequent dowels) are compared. An animal can delay gnawing on the first dowel until pharmacologic sedation has worn off and/or analgesia has taken effect without influencing the gnaw time for the second or subsequent dowels. Thus, the device accommodates pharmacokinetic differences between animals and pre-empts intractable difficulties with pharmacologic sedation, titration and analgesic onset.

A pharmacologic motor effect is less likely to corrupt the outcome variable since the first dowel acts as a prerequisite minimum motor verification task. For example, morphine reversal of pain is the gold standard against which novel analgesics are tested. However, morphine, like all opiates, has a sedative effect and an excitatory phase after induction. Accordingly, oral function can be drastically affected by such side effects. Our method allows the animal to pass through the sedative or excitatory phase before the outcome variable is measured. The animal will start its own clock for the outcome measure (the second or subsequent dowels) by first accomplishing the minimum motor verification task (severing the first dowel). Once it severs the first dowel, it has demonstrated progression beyond the motor effects of a drug being tested. Our method is not prone to false positives when evaluating the efficacy of sedating analgesics since sedation and analgesia produce opposite test outcomes in our invention. In most reflexive assays, sedation and analgesia produce a similar test result. For example, in the paw withdrawal assay, sedation and analgesia both increase withdrawal threshold. Without a motor verification task, other operant assays such as the mouse facial-thermal-operant assay (Neubert, J. K., et al., Mol Pain, 2008. 4:43) are likely to produce a false negative when evaluating sedating analgesics since the sedative effect alone can attenuate the operant behavior.

Appetite is less likely to affect the outcome variable in the invention because animals are confined for a relatively brief period in the tube without food. Moreover, the gnawing behavior that we measure does not involve consumption even though it engages most of the orofacial complex used for mastication (chewing). The rodent does not consume debris from the dowel since the animal instinctually occludes the oral cavity with the tongue, cheeks and lips behind the incisors while gnawing By our method, routine orofacial function in the animal involving most of the masticatory complex produces pain resulting from a clinically relevant pathology such as masseter myositis or oral cancer. After development of allodynia (pain), the animal voluntarily limits orofacial function in our device. Moreover the device can quantify and the investigator can compare dysfunction and thus nociception (pain) resulting from different pathologies. Analgesics restore gnawing function in our device in a manner similar to analgesic rescue seen in patients with pain-induced dysfunction. Studies on patients with TMJ disorders and masticatory muscle pain demonstrate that both the character and duration of oral function is critical in determining the amount of pain that a patient experiences. By our method, the animal is required to perform the task over an extended period as might be experienced during the daily oral functioning of a patient. Our assay and method is not dependent on appetite, subjective behavioral interpretation, laborious techniques or animal observation. It is objective and standardized so that all results are directly comparable across laboratories and can be employed by personnel with only basic rodent handling experience.

DETAILED DESCRIPTION OF THE INVENTION

Figure 1:
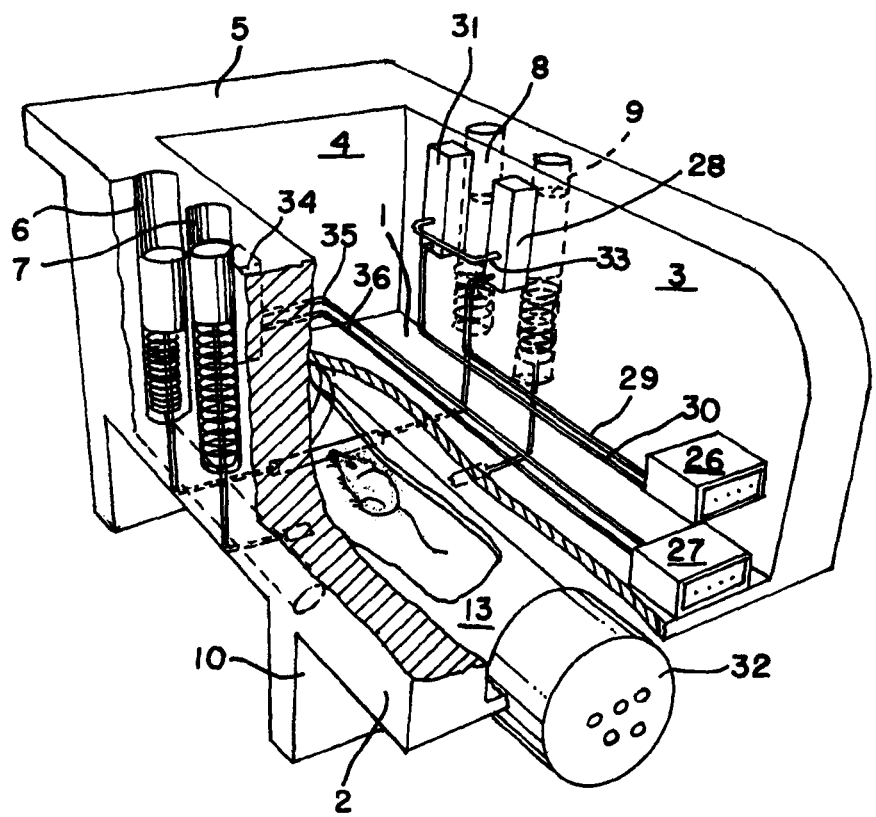
FIG. 1 is a perspective view of the device according to this invention.
Figure 2:
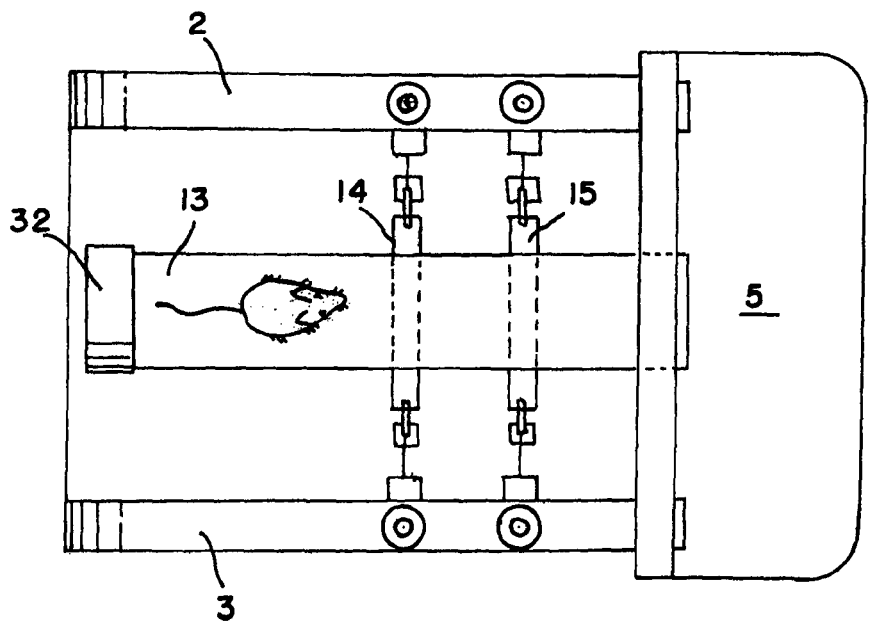
FIG. 2 is a bottom plan view thereof.

In the drawings and with particular reference to FIG. 1, the oral function and dysfunction quantification device is shown and includes bottom wall 1 with spaced side walls 2 and 3 extending upwardly from the side edges thereof. Rear wall 4 is secured to the end edges of bottom wall 1 and side walls 2 and 3 with shelf 5 extending outwardly therefrom. Cylinders 6 and 7 are disposed within side wall 2 and, in similar fashion, cylinders 8 and 9 are disposed within side wall 3. Also, stabilizing leg 10 is secured to the underside of bottom wall 1.

Figure 3:
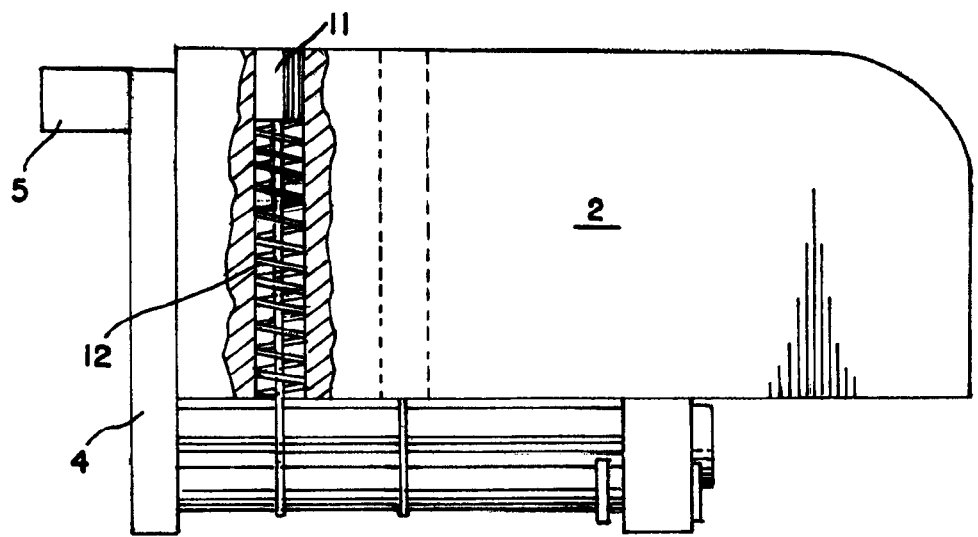
FIG. 3 is a side elevational view thereof with a portion of the side wall broken away.

Contained within each cylinder 6-9 is a piston arrangement and, since the structure is the same for each cylinder, only one is shown in detail in FIG. 3. More specifically, a piston 11 is disposed within each cylinder 6-9 with compression spring 12 disposed below piston 11 such that piston 11 is biased upwardly, as viewed in FIG. 3.

Figure 4:
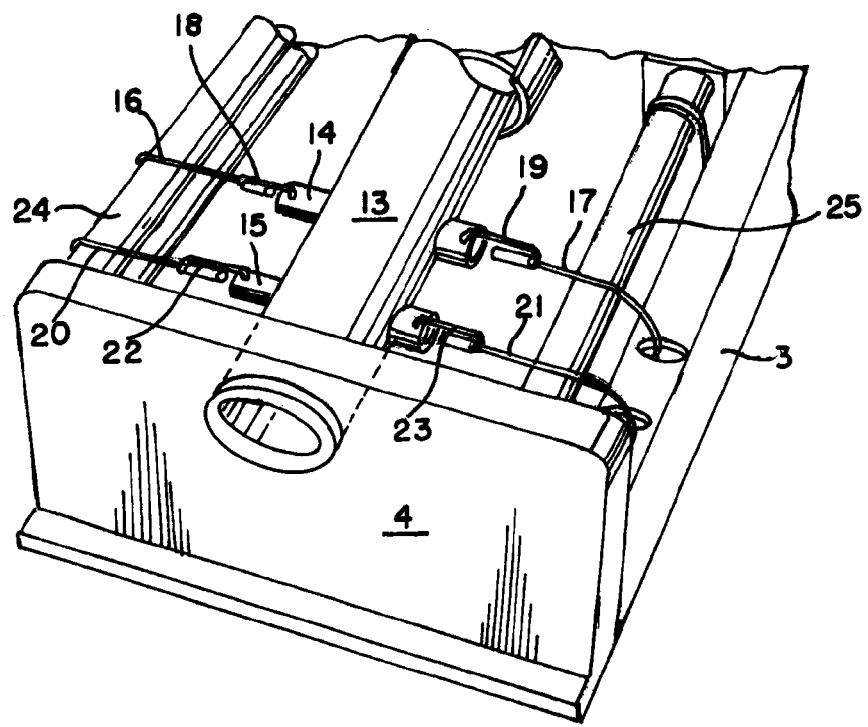
FIG. 4 is a perspective view from the bottom of the device.
Figure 5:
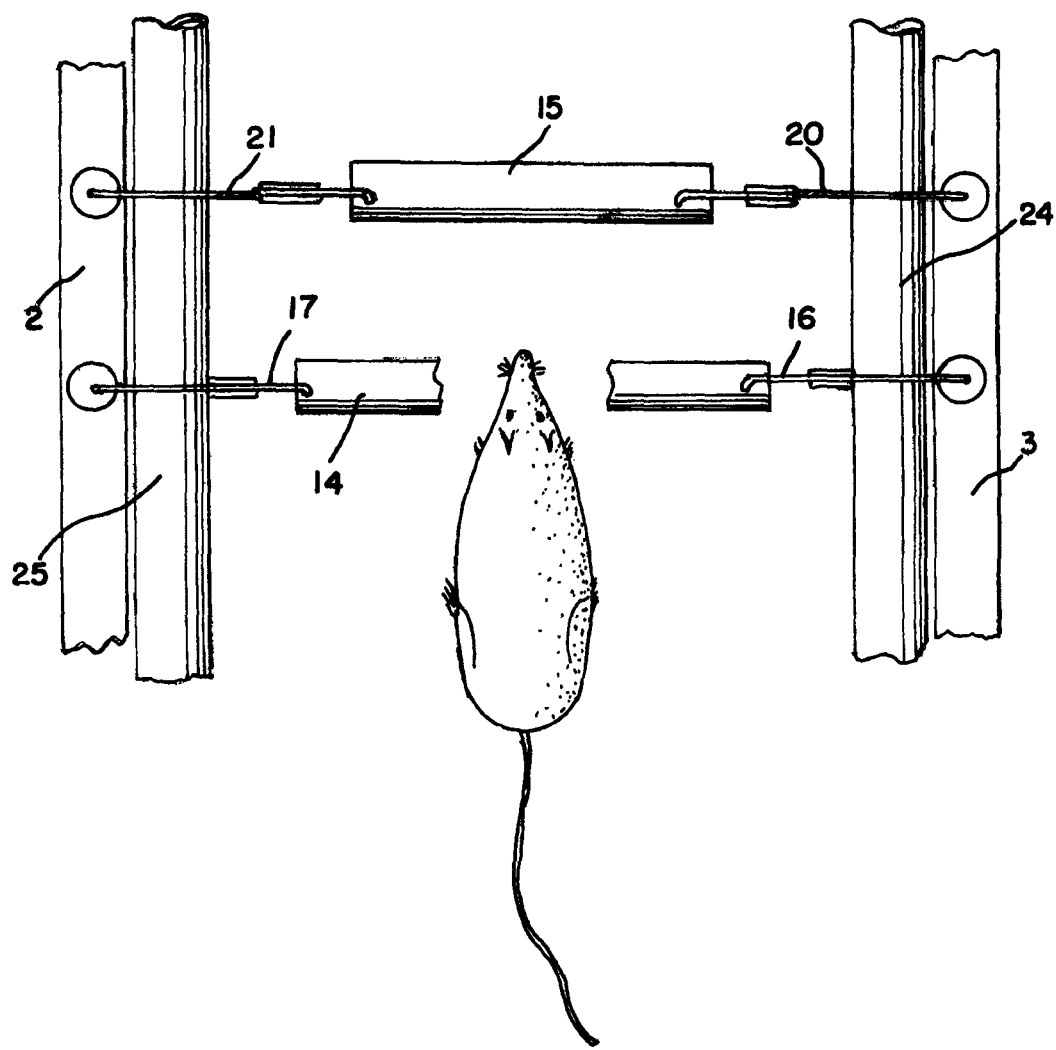
FIG. 5 is a partial top plan view depicting operation of the device.

According to this invention, confinement tube 13 extends longitudinally through the device. Spaced generally parallel, dowels 14 and 15 extend, respectively, through apertures formed in confinement tube 13 with the ends thereof projecting outwardly of confinement tube 13. Cables 16 and 17 are secured, respectively, to the ends of dowel 14 respectively, by means of hooks 18 and 19. In similar fashion, cables 20 and 21 are secured, respectively, to the ends of dowel 15 by means, respectively, of hooks 22 and 23. As best viewed in FIGS. 4 and 5, cables 16 and 20 extend around rod 24 and, similarly, cables 17 and 21 extend around rod 25. Each cable 16, 17, 20 and 21 then extends upwardly and is attached to the bottom of the respective piston 11 disposed in cylinders 6-9.

As best viewed in FIG. 1, timers 26 and 27 are attached to side wall 3. Further, timer 26 is connected to timer switches 28 and 31, associated with respective cylinders 9 and 8, by means of wires 29 and 30. Further, timer switches 28 and 31 are electrically connected with wire 33. Finally, timer 27 is connected to timer switch 34, associated with cylinder 7, by means of wires 35 and 36. To complete the basic elements of the device, perforated end cap 32 is positioned on the entry end of confinement tube 13. Timers 26 and 27 are suitably energized by a battery or other appropriate means, as is well known.

In operation and according to this invention, a laboratory animal, such as a mouse or rat, is introduced into confinement tube 13 and end cap 32 is placed over the end of confinement tube 13 to prevent escape of the mouse. Timer 27 is then manually actuated to initiate the timing sequence and, due to confinement anxiety, the laboratory animal is motivated to begin gnawing through dowel 14 to the point where dowel 14 is completely severed thereby causing cables 16 and 17 to retract due to the action of associated springs 12 causing dowel 14 to separate into two parts whereby piston 11, disposed in cylinder 7, is urged upwardly by means of spring 12 such that the movement of piston 11 disposed in cylinder 7 causes timer switch 34 to stop the timing sequence of timer 27 thereby registering elapsed time. Simultaneously, the upward movement of piston 11 disposed in cylinder 9 caused by spring 12 actuates timer switch 28 causing timer 26 to initiate a timing sequence.

Again, due to confinement anxiety, the mouse is motivated to begin gnawing on dowel 15 whereby the process is repeated and dowel 15 is severed to cause spring-biased cables 20 and 21 to retract and pull the two severed parts of dowel 15 apart. This causes piston 11 disposed within cylinder 8 to move upwardly and actuate timer switch 31 thereby stopping the timing sequence and digitally displaying the expired time on timer 26. By this means, the precise amount of time it took the animal to gnaw through dowel 15 is registered. The laboratory animal then is able to escape confinement tube 13 and enter an appropriate cage surrounding the device.

The invention is adaptable for use with only a single dowel 14 and no subsequent dowels whereby the time to gnaw through and sever the first and only dowel is recorded. More than two dowels in series can be used with this invention in an augmented configuration that includes appropriate repetition of similar dowel retraction architecture, switches, timers, and a similar serial timing circuit configuration whereby the timing sequence for each successive dowel is initiated by the severing of the previous dowel.

Therefore, by this invention, a method utilizing a quantification device is provided that incorporates automatic timing into a device in which gnawing performance is not dependent on animal appetite and by which the end result is objective and not dependent on investigator observation since the laboratory animal self starts the timing sequence for each dowel subsequent to the first and self stops each timing sequence.

The invention claimed is:

1. A method of quantifying oral function and dysfunction comprising the steps of:
   confining a laboratory animal to a confinement tube;
   limiting forward progress by means of a first dowel extending through said confinement tube;
   determining the elapsed time for said animal to sever said first dowel;
   positioning a second dowel through said confinement tube generally parallel to said first dowel and spaced therefrom;
   determining the elapsed time between the severance of said first dowel and said animal's severance of said second dowel;
   wherein the determined elapsed time quantifies the oral function and dysfunction.

2. A method according to claim 1 wherein said elapsed time to sever said first dowel is determined by means of a timer.

3. A method according to claim 2 wherein said timer is manually activated.

4. A method according to claim 2 wherein the severance of said first dowel deactivates said timer.

5. A method according to claim 1 wherein said elapsed time between the severance of said first dowel and the severance of said second dowel is determined by means of a second timer.

6. A method according to claim 5 wherein the severance of said first dowel activates said second timer.

7. A method according to claim 5 wherein the severance of said second dowel deactivates said second timer.

8. A method according to claim 1 wherein one or more dowels are respectively spaced from said second dowel remote from said first dowel.

* * * * *